(12) United States Patent
Chen et al.

(10) Patent No.: US 9,145,376 B2
(45) Date of Patent: Sep. 29, 2015

(54) QUINAZOLINONE INHIBITORS OF DYNEIN

(75) Inventors: James K. Chen, Mountain View, CA (US); Tarun M. Kapoor, New York, NY (US); Ari J. Firestone, San Mateo, CA (US); Joshua S. Weinger, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 13/980,527

(22) PCT Filed: Jan. 18, 2012

(86) PCT No.: PCT/US2012/021639
§ 371 (c)(1),
(2), (4) Date: Jul. 18, 2013

(87) PCT Pub. No.: WO2012/099916
PCT Pub. Date: Jul. 26, 2012

(65) Prior Publication Data
US 2013/0296349 A1    Nov. 7, 2013

Related U.S. Application Data

(60) Provisional application No. 61/434,545, filed on Jan. 20, 2011.

(51) Int. Cl.
*A61K 31/57* (2006.01)
*C07D 239/91* (2006.01)
*A61K 31/517* (2006.01)

(52) U.S. Cl.
CPC ............ *C07D 239/91* (2013.01); *A61K 31/517* (2013.01)

(58) Field of Classification Search
CPC ... A01N 43/54; A61K 31/517; C07D 239/72; C07D 401/02
USPC ................. 514/266.2; 544/283, 284
See application file for complete search history.

(56) References Cited

U.S. PATENT DOCUMENTS

2005/0080138 A1    4/2005    Guicherit et al.

FOREIGN PATENT DOCUMENTS

WO    2009/102864 A1    8/2009

OTHER PUBLICATIONS

Pallai et al., Mol Pharm. 2010, 77(5), 724-733.*
Hyman et al., Proceedings of the National Academy of Sciences of the United States of America (2009), 106(33), 14132-14137,S14132/1-S14132/21 CODEN: PNASA6; ISSN: 0027-8424.*
Volovenko et al (1994).*
Pinedo et al (2000) McMahon et al (2000).*
International Search Report for International Application No. PCT/US2012/021639, dated Jan. 18, 2012.
Dar'in et al. "Cyclocondensation of [alpha]-acylacetamidines with esters of 2-flouro-5-nitrobenzoic and 4-chloro-2-methyl-5-pyrimidinecarboxylic acids" Chemistry of Heterocyclic Compounds, vol. 44, No. 4, Apr. 1, 2008, pp. 461-465.
Haber et al. "Heterocyclensynthesen mit 5-Phenyl-isoxazoliumsalzen; Synthese and Eigenschaften von 2-Phenacyliden-chinazolin-4-onen" Zeitschrift fur Chemie, vol. 27, No. 9, Sep. 1, 1987, pp. 336-337.
Pillai et al. "A Cell-Based High-Throughput Screen Validates the Plasmodial Surface Anion Channel As an Antimalarial Target" Molecular Pharmacology, vol. 77, No. 5, May 1, 2010, pp. 724-733.
Hyman et al. "Small-molecule inhibitors reveal multiple strategies for Hedgehog pathway blockade" Proceedings of the National Academy of Sciences, vol. 106, No. 33, Aug. 18, 2009, pp. 14132-14137.
Volovenko et al. "2-(3,4-Dihydro-4-oxo-2-quinazolinyl)aceto nitriles in the Synthesis of New Condensed Pyrimidines" Synthesis, vol. 2004, No. 16, Jan. 1, 2004, pp. 2659-2664.
"A Facile Method for the Synthesis of Novel Quinazolinone Compounds" Synthetic Communications, vol. 26, No. 3, Aug. 21, 2006, pp. 475-482.
Rudin et al. "Treatment of Medulloblastoma with Hedgehog Pathway Inhibitor GDC-0449" N. Engl.J.Med 361, 2009, pp. 1173-1178.
Von Hoff et al. "Inhibition of the Hedgehog Pathway in Advanced Basal-Cell Carcinoma" N. Engl.J.Med 361, 2009, pp. 1164-1172.

* cited by examiner

*Primary Examiner* — Paul V Ward
(74) *Attorney, Agent, or Firm* — Heslin, Rothenberg, Farley & Mesiti, P.C.

(57) ABSTRACT

Compounds of formula (I) in which $R_3$ is chosen from hydrogen, cyano, nitro, acetyl and $C(=O)NH_2$, and Ar is optionally substituted monocyclic or bicyclic aryl or heteroaryl, are useful as antitumor agents.

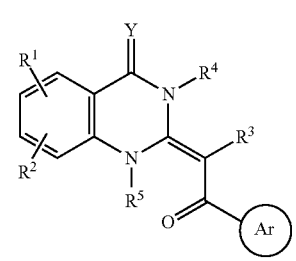

12 Claims, 1 Drawing Sheet

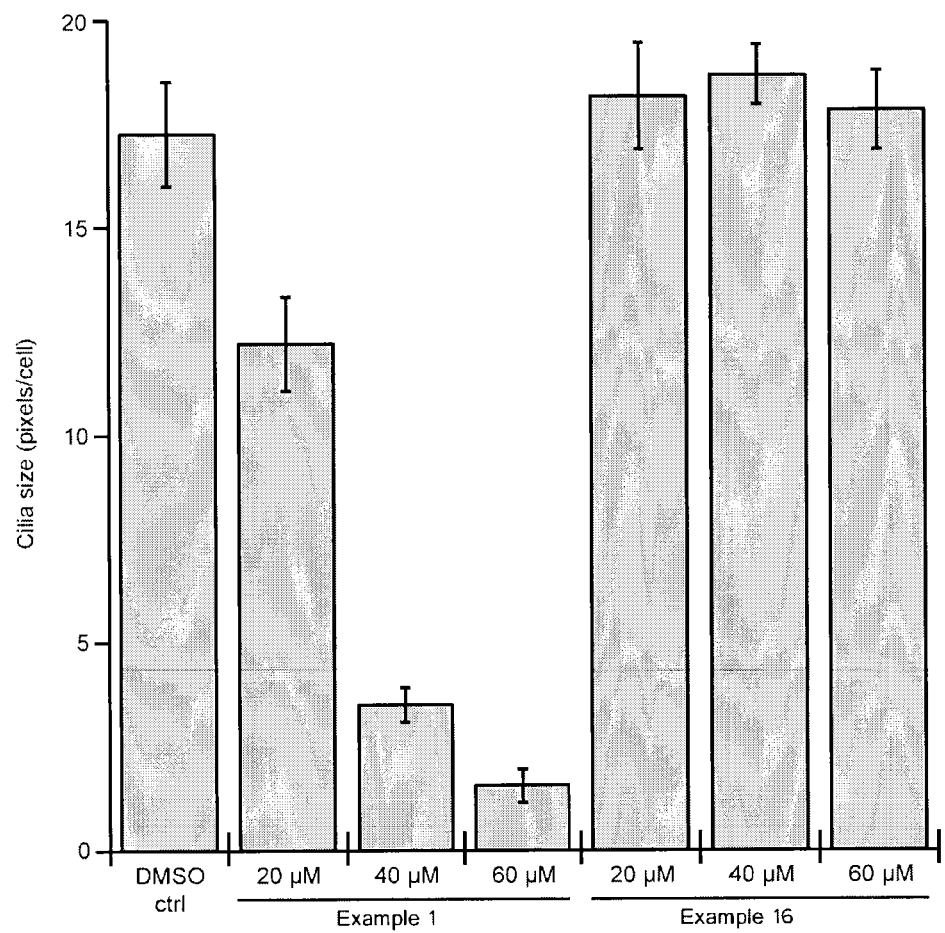

QUINAZOLINONE INHIBITORS OF DYNEIN

CROSS-REFERENCE TO RELATED APPLICATIONS

This application is a national stage filing under section 371 of International Patent Application No. PCT/US12/021639 filed on Jan. 18, 2012 and published in English as WO 2012/099916 on Jul. 26, 2012. PCT/US12/021639 claimed priority from U.S. provisional application 61/434,545, filed Jan. 20, 2011. The entire content of each prior application is hereby incorporated by reference.

FEDERALLY SPONSORED RESEARCH

The following invention was made with government support under contracts numbers R01_CA136574, R01_GM71772 and R01_GM65933 awarded by the National Cancer Institute and the National Institutes of Health. The Government has certain rights in this invention.

FIELD OF THE INVENTION

The invention relates to 4-oxo-3,4-dihydroquinazolin-2 (1H)-ylidene derivatives that are selective inhibitors of members of the family of AAA+ ATPases. The compounds are useful as antitumor agents and as probes of the function of dynein-dependent systems.

BACKGROUND OF THE INVENTION

The AAA+ (ATPases associated with diverse cellular activities) superfamily of enzymes couples ATP hydrolysis with the generation of mechanical force to regulate diverse aspects of prokaryote and eukaryote biology. These complex proteins typically form ring-shaped hexamers with a central pore, and ATP-dependent conformational changes that propagate through these molecular machines can promote DNA replication, the disassembly of membrane-fusing complexes during organelle biogenesis and vesicular transport, the trafficking of cellular cargos along microtubules, and the unfolding of proteins for proteolysis. One of the subclasses of AAA+ ATPases includes dynein 1 and dynein 2. Cytoplasmic dynein 1 acts in concert with dynactin and the nuclear protein NuMA to crosslink and focus the minus ends of microtubules within the mitotic spindle. These actions create the canonical fusiform shape and localize γ-tubulin-containing, microtubule-nucleating complexes to the spindle poles. Cytoplasmic dynein 1 inhibition, by blocking antibodies or dominant negative constructs, disrupts mitotic spindle assembly, resulting in splayed microtubule ends and reduced γ-tubulin recruitment. Dynein 2 is integral in protein trafficking mechanisms within the primary cilium, where it is involved in moving macromolecules along the axoneme. Intraflagellar retrograde trafficking, utilizes cytoplasmic dynein 2 and the IFTA complex. Small-molecule AAA+ ATPase inhibitors, particularly those that can act rapidly and reversibly are therefore much needed, both as probes of dynein function and as potential antitumor agents.

SUMMARY OF THE INVENTION

In one aspect, the invention relates to compounds of formula I:

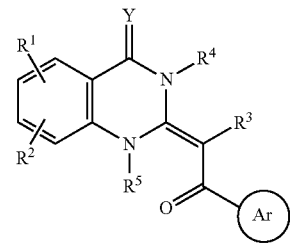

wherein
$R^1$ and $R^2$ are independently chosen from hydrogen, halogen, $(C_1-C_{10})$hydrocarbon, —O—$(C_1-C_6)$alkyl, fluoro$(C_1-C_6)$alkyl, —O—$(C_1-C_6)$fluoroalkyl, hydroxy, methylenedioxy, ethylene dioxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino, $(C_1-C_6)$acylamino and -A-$R^{10}$; wherein A is a $(C_1-C_6)$hydrocarbon and $R^{10}$ is chosen from —O—$(C_1-C_6)$alkyl, fluoro$(C_1-C_6)$alkyl, —O—$(C_1-C_6)$fluoroalkyl, hydroxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino and $(C_1-C_6)$acylamino;
$R^3$ is chosen from hydrogen, cyano, nitro, acetyl and —C(=O)$NH_2$;
$R^4$ and $R^5$ are independently chosen from hydrogen and methyl; and
Y is O or $NR^8$;
$R^8$ is chosen from hydrogen and $(C_1-C_7)$hydrocarbon and Ar is optionally substituted monocyclic or bicyclic aryl or heteroaryl.

In another aspect, the invention relates to a method of inhibiting the growth of a solid tumor comprising bringing said solid tumor into contact with a compound of formula I.

In another aspect, the invention relates to method of inhibiting a dynein comprising bringing said dynein into contact with a compound of formula II

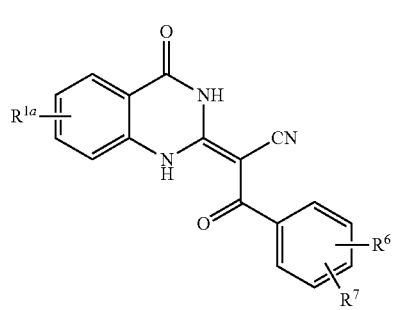

wherein
$R^{1a}$ is hydrogen or halogen; and
$R^6$ and $R^7$ are halogen.

In another aspect, the invention relates to a method of inhibiting retrograde cilial transport comprising bringing a cell having at least one cilium into contact with a compound of formula II.

BRIEF DESCRIPTION OF THE DRAWINGS

FIG. 1 is a bar graph showing cilia size as a function of drug concentration for two examples according to the invention.

DETAILED DESCRIPTION OF THE INVENTION

Antitumor compounds of the invention fall into two primary classes: compounds of general formula I, which inhibit hedgehog signaling and thereby inhibit tumor growth, and a subgenus II, which selectively inhibit dynein and also inhibit tumor growth, but by a different mechanism. The inhibition of hedgehog signaling has been shown to be effective in vivo in treating solid tumors, particularly basal cell carcinoma, glioblastoma and medulloblastoma. For example, Rudin et al. [*N. Engl. J. Med* 361, 1173-1178 (2009)] demonstrated that administration to a human patient of GDC-0449, a small molecule inhibitor of the hedgehog pathway, resulted in regression of medulloblastoma. Similarly, Von Hoff et al. [*N. Engl. J. Med* 361, 1164-1172 (2009)] administered GDC-0449 to 33 human patients with basal cell carcinoma and observed clinically significant response.

In one aspect, the invention relates to compounds of formula I:

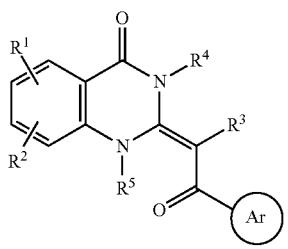

In these compounds, $R^1$ and $R^2$ are independently chosen from hydrogen, halogen, $(C_1-C_{10})$hydrocarbon, —O—$(C_1-C_6)$alkyl, fluoro$(C_1-C_6)$alkyl, —O—$(C_1-C_6)$fluoroalkyl, hydroxy, methylenedioxy, ethylenedioxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino, $(C_1-C_6)$acylamino and -A-$R^{10}$; wherein A is a $(C_1-C_6)$hydrocarbon and $R^{10}$ is chosen from —O—$(C_1-C_6)$alkyl, fluoro$(C_1-C_6)$alkyl, —O—$(C_1-C_6)$fluoroalkyl, hydroxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino and $(C_1-C_6)$acylamino. In some embodiments, $R^2$ is H and $R^1$ is chosen from H, halogen, methoxy, aminopropargyl and acetamidopropargyl. In some embodiments, $R^1$ is H or halogen.

In compounds of the genus I, $R^3$ may be hydrogen, cyano, nitro, acetyl or —C(=O)NH$_2$. In some embodiments, $R^3$ is cyano.

In compounds of the genus I, $R^4$ and $R^5$ may be hydrogen or methyl; and in many embodiments, they will both be hydrogen.

The compounds of formula I may be divided into two subgenera based on the value of Y. In one subgenus Y is $NR^8$; in the other subgenus Y is O:

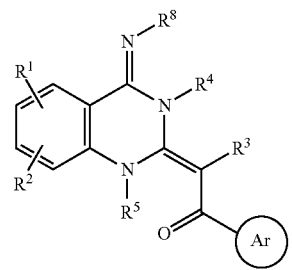

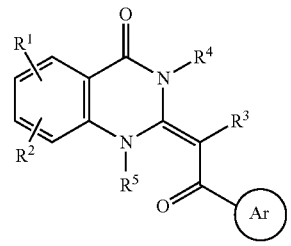

In compounds of the genus I (i.e. structures Ia and Ib), Ar is optionally substituted monocyclic or bicyclic aryl or monocyclic or bicyclic heteroaryl. Examples of aryl and or heteroaryl, that may optionally substituted, include, e.g., phenyl, naphthyl, imidazole, pyridine, indole, thiophene, benzopyranone, thiazole, furan, benzimidazole, quinoline, isoquinoline, quinoxaline, pyrimidine, pyrazine, tetrazole and pyrazole. In some embodiments, Ar is chosen from phenyl, naphthyl, thiophenyl, furanyl, pyrrolyl, and pyridinyl, any of which may be optionally substituted with from one to three substituents independently chosen from halogen, $(C_1-C_{10})$hydrocarbon, fluoro$(C_1-C_6)$alkyl, —O—$(C_1-C_6)$fluoroalkyl, —CN, nitro, $(C_1-C_6)$alkoxycarbonyl and $(C_1-C_6)$acyl. In some embodiments, Ar is phenyl substituted with from one to three halogens. In some embodiments, Ar is 2,4-dichlorophenyl or 3,4-dichlorophenyl. In some embodiments of Ia, $R^8$ is hydrogen or methyl.

In some embodiments, $R^3$ is CN; $R^2$, $R^4$ and $R^5$ are H; and $R^1$ is chosen from H and halogen. In some embodiments, $R^3$ is CN; $R^2$, $R^4$ and $R^5$ are H; $R^1$ is chosen from H and halogen and Ar is phenyl substituted with from one to three halogens. Among these are the compounds of formula II

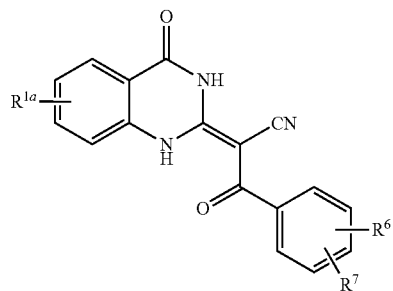

wherein $R^{1a}$ is hydrogen or halogen; and $R^6$ and $R^7$ are halogen, which are selective for dynein inhibition.

All of the compounds falling within the foregoing parent genus and its subgenera are useful as modulators of the hedgehog pathway and/or dynein, but not all the compounds are novel. In particular, a search of the literature indicates that when Ar is 2,4-dichlorophenyl and $R^1$, $R^2$, $R^4$ and $R^5$ are hydrogen, the compound in which $R^3$ is cyano cannot be claimed [see PCT WO2009/102864, page 53, structure 18]. It may be found upon examination that additional species and genera not presently excluded are not patentable to the inventors in this application. In that case, the exclusion of species and genera from applicants' claims are to be considered artifacts of patent prosecution and not reflective of the inventors' concept or description of their invention. The invention, in a composition aspect, is all compounds of formula I except those that are in the public's possession.

DEFINITIONS

Throughout this specification the terms and substituents retain their definitions.

Alkyl is intended to include linear, branched and cyclic hydrocarbon structures and combinations thereof. A combination would be, for example, cyclopropylmethyl. Any hydrocarbon in which all carbons are essentially $sp^3$ hybridized and no carbons are $sp^2$ or sp hybridized is considered alkyl. To be perfectly clear, when a substituent is $(C_1-C_6)$ alkyl, it is meant that it can be a straight chain (for instance, methyl or ethyl), a branched chain (e.g., t-butyl), a cycloalkyl (for instance, cyclopropyl or cyclobutyl), or a combination (e.g., methylcyclopropyl). If a substituent is described more specifically, however, it takes on that definition; for instance, recitation of "cycloalkyl" refers only to a cyclic alkyl and not a linear or combination alkyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl, adamantyl and the like.

Alkoxy or alkoxyl refers to alkyl groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an aryl ring attached to an alkyl residue in which the point of attachment to the parent structure is through the alkyl. Examples are benzyl, phenethyl and the like. Heteroarylalkyl means an a heteroaryl ring attached through an alkyl residue to the parent structure. Examples include, e.g., pyridinylmethyl, pyrimidinylethyl and the like.

$C_1$ to $C_{10}$ hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, cyclopropylmethyl, cyclobutylmethyl, allyl and camphoryl.

Unless otherwise specified, the term "carbocycle" is intended to include ring systems in which the ring atoms are all carbon but of any oxidation state. Thus $(C_3-C_{10})$ carbocycle refers to both non-aromatic and aromatic systems, including such systems as cyclopropane, cyclobutane, cyclopentane, cyclohexane, benzene, cyclohexene and cyclohexadiene; $(C_8-C_{12})$ carbopolycycle refers to such systems as norbornane, decalin, indane, adamantane and naphthalene. Carbocycle, if not otherwise limited, refers to monocycles, bicycles and polycycles.

Heterocycle means a cycloalkyl or aryl residue in which one to three of the carbons is replaced by a heteroatom such as oxygen, nitrogen or sulfur. Heteroaryls form a subset of heterocycles. Examples of heterocycles include pyrrolidine, pyrazole, pyrrole, imidazole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, pyrazine, thiophene, furan, oxazole, oxazoline, isoxazole, dioxane, tetrahydrofuran and the like.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(═O)O-alkyl], alkoxycarbonylamino [HNC(═O)O-alkyl], carboxamido [—C(═O)NH$_2$], alkylaminocarbonyl [—C(═O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). Although in most cases of "optionally substituted" residues, 1, 2 or 3 hydrogen atoms are replaced with a specified radical, in the case of fluoroalkyl residues, more than three hydrogen atoms can be replaced by fluorine; indeed, all available hydrogen atoms could be replaced by fluorine, e.g. perfluoropropyl.

The compounds described herein may contain one or more asymmetric centers in their side chains, and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound"—unless expressly further limited—is intended to include salts of that compound. In a particular embodiment, the term "compound of formula I" refers to the compound or a pharmaceutically acceptable salt thereof.

It will be recognized that the compounds of this invention can exist in radiolabeled form, i.e., the compounds may contain one or more atoms containing an atomic mass or mass number different from the atomic mass or mass number usually found in nature. Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include, for example, $^{2}H$, $^{3}H$, $^{11}C$, $^{13}C$, $^{14}C$, $^{15}N$, $^{35}S$, $^{18}F$, $^{36}Cl$, $^{123}I$, $^{125}I$, $^{131}I$ and $^{133}I$. Compounds that contain those radioisotopes and/or other radioisotopes of other atoms are within the scope of this invention. Compounds containing $^{3}H$, $^{14}C$ and iodine radioisotopes are particularly preferred for their ease in preparation and detectability. Compounds that contain isotopes $^{11}C$, $^{13}N$, $^{15}O$ and $^{18}F$ are well suited for positron emission tomography. Radiolabeled compounds of formulae I and II of this invention can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

When the compounds of formula I or II are to be employed as antitumor agents in vivo, they may be administered as the raw chemical, but it is preferable to present them as a pharmaceutical composition. According to a further aspect, the present invention provides a pharmaceutical composition comprising a compound of formula I or II or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof. The compositions may be formulated for oral, topical or parenteral administration. For example, they may be given intravenously, intraarterially, subcutaneously, and directly into the CNS—either intrathecally or intracerebroventricularly.

Formulations include those suitable for oral, parenteral (including subcutaneous, intradermal, intramuscular, intravenous and intraarticular), rectal and topical (including dermal, buccal, sublingual and intraocular) administration. The compounds are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. The formulations may conveniently be presented in unit dosage form and may be prepared by any of the methods well known in the art of pharmacy. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as herein below recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

As used herein, the terms "treatment" or "treating," or "palliating" or "ameliorating" refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological systems associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological systems of a disease, even though a diagnosis of this disease may not have been made.

ABBREVIATIONS

The following abbreviations and terms have the indicated meanings throughout:
Ac=acetyl
Boc=t-butyloxy carbonyl
BOP=benzotriazol-1-yloxy-tris(dimethylamino)phosphonium hexafluorophosphate
Bu=butyl
BSA=bovine serum albumin
c-=cyclo
DCM=dichloromethane=methylene chloride=$CH_2Cl_2$
DIEA=diisopropylethylamine
DMEM=Dulbecco's modified Eagle medium
DMF=N,N-dimethylformamide
DMSO=dimethyl sulfoxide
DTT=dithiothreitol EtOAc=ethyl acetate
EtOH=ethanol
GC=gas chromatography
HOAc=acetic acid
Me=methyl
MTBE=methyl t-butyl ether
PBS=phosphate buffered saline
PEG=polyethylene glycol
PMSF=phenylmethanesulfonyl fluoride
Ph=phenyl
PhOH=phenol
PVDF=polyvinylidene fluoride
rt=room temperature
sat'd=saturated
s-=secondary
SDS=sodium dodecylsulfate
t- or tert-=tertiary
TBDMS=t-butyldimethylsilyl
TFA=trifluoroacetic acid
THF=tetrahydrofuran
TMS=trimethylsilyl
tosyl=p-toluenesulfonyl The conversion of chemical potential energy into mechanical force by AAA+ATPases is integral to a myriad of cellular processes, as discussed above in the Background section. Investigations into the dynamic functions of this protein superfamily would benefit from small-molecule modulators, yet inhibitors of these complex, oligomeric mechanoenzymes have remained elusive. This patent application describes a genus of 4-oxo-3,4-dihydroquinazolin-2(1H)-ylidene derivatives that are selective inhibitors of members of the family of AAA+ ATPases. It also describes a subgenus, which the inventors call "ciliobrevins", which are selective inhibitors of cytoplasmic dynein, a motor AAA+ ATPase. It is here disclosed that ciliobrevins perturb trafficking within the primary cilium, leading to the malformation of the cilia and the abrogation of cilia-dependent signaling mechanisms such as those that regulate the Hedgehog pathway. Ciliobrevins also prevent spindle pole focusing in mitotic cells and melanosome aggregation in cultured melanophores. These cellular phenotypes are consistent with the pharmacological inhibition of cytoplasmic dyneins 1 and 2, and the experiments described herein demonstrate the ability of ciliobrevins to selectively block dynein-dependent microtubule gliding in vitro. In addition to their utility in vivo as antitumor agents, ciliobrevins will therefore be useful reagents in vitro for studying cellular processes that employ this minus-end-directed microtubule motor and may guide the development of additional AAA+ ATPase superfamily inhibitors.

Cell-based, phenotypic screening of small molecules is a powerful technique for discovering small-molecule modulators of complex cellular functions. A high-throughput screen for inhibitors of the Hedgehog (Hh) pathway, a key mediator of embryonic development, stem cell self-renewal, and oncogenesis, was designed to identify compounds that act downstream of Smoothened (Smo), a G protein-coupled receptor-like transducer of the Hh signal, and a number of dihydroquinazolinones were identified that blocked Hh pathway activation in cells lacking Suppressor of Fused (Sufu), a negative regulator of the Gli transcription factors that induce Hh target gene expression.

Syntheses

Benzoyl dihydroquinazolinone example 24 was purchased from Chembridge; all other structural derivatives were synthesized as described below. All chemicals used for organic synthesis were purchased from Sigma-Aldrich or Acros and used without further purification. Anhydrous conditions were maintained under nitrogen using standard Schlenk line techniques and oven-dried glassware. $^1H$ NMR spectra were taken on Varian Inova 300, 400 and 500 MHz spectrometers in DMSO-$d_6$, and chemical shifts are reported as parts per million (ppm) downfield of the DMSO solvent peak. High-resolution mass spectrometry (HRMS) data were obtained on a Micromass Q-TOF hybrid quadrupole liquid chromatography-mass spectrometer at the Stanford University Mass Spectrometry Facility.

Example 1

3-(2,4-dichlorophenyl)-3-oxo-2-(4-oxo-3,4-dihydroquinazolin-2(1H)-ylidene)propanenitrile ["ciliobrevin A"]

2-Cyanoethanethioamide (1.00 g, 10.0 mmol) and bromoethane (821 µL, 11.0 mmol) were added to an ethanolic solution of sodium ethoxide (11.5 mmol, 5.3 mL). The resulting mixture was stirred for 6 hours, 2-aminobenzoic acid (1.50 g, 10.9 mmol) was added, and the reaction was refluxed overnight with stirring. A solid precipitate formed upon cooling of the reaction mixture, which was recovered by vacuum filtration and washed sequentially with ethanol, water, ethanol, and diethyl ether. The solid was then dried to yield 2-(4-oxo-3,4-dihydroquinazolin-2-yl)acetonitrile (872 mg, 47%). $^1$NMR (400 MHz, DMSO-$d_6$) δ ppm 4.17 (s, 2H), 7.53 (t, J=7.5 Hz, 1H), 7.68 (d, J=7.9 Hz, 1H), 7.83 (t, J=7.8 Hz, 1H), 8.10 (dd, $J_1$=7.9 Hz, $J_2$=1.2 Hz, 1H).

To solution of 2-(4-oxo-1.4-dihydroquinazolin-2-yl)acetonitrile (202 mg, 1.09 mmol) and triethylamine (167 µL, 1.20 mmol) in dioxane (8 mL) was added 2.4-dichlorobenzoyl chloride (152 µL, 1.09 mmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield ciliobrevin A (1) (213 mg, 53%). $^1H$ NMR (400 MHz, DMSO-$d_6$) δ ppm 7.46-7.50 (m, 1H), 7.52 (d. 1=8.2 Hz, 1H), 7.56 (dd, $J_1$=8.2, $J_2$=1.9 Hz, 1H), 7.77 (d, J=2.0 Hz, 1H), 7.83-7.88 (m, 2H), 8.07 (d, J=8.1 Hz, 1H). $^{13}C$ NMR (500 MHz, DMSO-$d_6$) δ ppm 71.74, 117.43, 117.54, 118.71, 125.92, 126.68, 127.66, 129.21, 129.66, 130.49, 134.85, 135.85, 138.15, 139.25, 155.01, 158.3, 188.75. HRMS (m/z): [M+ calc. for $C_{17}H_9N_3O_2Cl_2Na$, 379.9970; observed, 379.9967.

Example 2

3-(4-chlorophenyl)-3-oxo-2-(4-oxo-3,4-dihydro-quinazolin-2(1H)-ylidene)propanenitrile To solution of 2-(4-oxo-1,4-dihydroquinazolin-2-yl)acetonitrile (54.2 mg, 293 μmol) and triethylamine (49.0 μL, 351 μmol) in dioxane (7 mL) was added 4-chlorobenzoyl chloride (45.1 μL, 351 μmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield analog 8 (59.9 mg, 63%). $^1$H NMR (500 MHz, DMSO-$d_6$) δ ppm 7.47 (t, J=7.6 Hz. 11-1), 7.57-7.60 (m, 2H), 7.72-7.75 (m, 2H), 7.84 (t. J=7.8 Hz, 1H), 7.89 (d, J=8.2 Hz, 1H) 8.06 (d, J=8.1 Hz, 1H). $^{13}$C NMR (500 MHz, DMSO-$d_6$) δ ppm 69.44, 117.31, 118.68, 118.73, 125.73, 126.65, 128.29, 129.54, 135.79, 135.88, 137.96, 156.02, 158.37, 189.76. HRMS (m/z): [M+Na]$^+$ calc. for $C_{17}H_{10}N_3O_2ClNa$, 346.0359; observed, 346.0359.

Example 10

3-(2-chlorophenyl)-3-oxo-2-(4-oxo-3,4-dihydro-quinazolin-2(1H)-ylidene)propanenitrile To solution of 2-(4-oxo-1,4-dihydroquinazolin-2-yl)acetonitrile (22.0 mg, 119 mmol) and triethylamine (18.2 μL, 131 mmol) in dioxane (3 mL) was added 2-chlorobenzoyl chloride (20.8 μL, 164 μmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield analog 6 (12.5 mg, 33%). $^1$H NMR (300 MHz, DMSO-$d_6$) δ ppm 7.43-7.52 (m, 4H), 7.52-7.57 (m, 1H), 7.81-7.87 (m, 2H), 8.06 (d, J=8.1 Hz, 1H). $^{13}$C NMR (500 MHz, DMSO-$d_6$) δ ppm 71.7, 117.41, 117.62, 118.73, 125.81, 126.68, 127.33, 128.22, 129.18, 129.57, 131.1, 135.81, 139.33, 155.12, 158.36, 189.89. HRMS (m/z): [M+Na]$^+$ calc. for $C_{17}H_{10}N_3O_2ClNa$, 346.0359; observed, 346.0373.

Example 16

3-oxo-2-(4-oxo-3,4-dihydroquinazolin-2(1H)-ylidene)-3-phenylpropanenitrile

To solution of 2-(4-oxo-1,4-dihydroquinazolin-2-yl)acetonitrile (42.8 mg, 231 mmol) and triethylamine (38.7 μL, 277 μmol) in dioxane (4 mL) was added benzoyl chloride (32.2 μL, 277 μmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield analog 2 (36.4 mg, 54%). $^1$H NMR (500 MHz, DMSO-$d_6$) δ ppm 7.47 (t, J=7.5 Hz, 1H), 7.49-7.53 (m, 2H), 7.54-7.58 (m, 1H), 7.70-7.73 (m, 2H), 7.84 (td, J$_1$=7.7 Hz, J$_2$=1.5 Hz, 1H), 7.89 (br. d, J=8.1 Hz, 1H), 8.06 (dd, J$_1$=8.1, J$_2$=1.5 Hz, 1H). $^{13}$C NMR (500 MHz, DMSO-$d_6$) δ ppm 69.3, 117.26, 118.57, 118.81, 125.65, 126.65, 127.59, 128.14, 131.22, 135.77, 139.26, 139.33, 156.12, 158.39, 191.18. HRMS (m/z): [M+Na]$^+$ calc. for $C_{17}H_{11}N_3O_2Na$, 312.0749: observed, 312.0735.

Example 17

3-(3-chlorophenyl)-3-oxo-2-(4-oxo-3,4-dihydro-quinazolin-2 (1H)-ylidene)propanenitrile To solution of 2-(4-oxo-1,4-dihydroquinazolin-2-yl)acetonitrile (152 mg, 0.820 mmol) and triethylamine (126 μL, 0.904 mmol) in dioxane (10 mL) was added 3-chlorobenzoyl chloride (116.3 μL, 0.904 mmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield analog 7 (172 mg, 65%). $^1$H NMR (400 MHz, DMSO-$d_6$) δ ppm 7.48 (t, J=7.5 Hz, 1H), 7.55 (t, J=7.8 Hz, 1H), 7.61-7.87 (m, 3H), 7.85 (t, J=7.6 Hz, 1H), 7.90 (d, J=8.2 Hz, 1H), 8.07 (d, J=8.2 Hz, 1H). $^{13}$C NMR (500 MHz, DMSO-$d_6$) δ ppm 69.62, 117.34, 118.62, 118.73, 25.78, 126.23, 26.65, 127.28, 130.22, 130.9, 132.88, 135.81, 141.15, 155.96, 158.36, 189.3. HRMS (m/z): [M+Na]$^+$ calc. for $C_{17}H_{10}N_3O_2ClNa$, 346.0359; observed, 346.0368.

Example 25

2-(5-chloro-4-oxo-3,4-dihydroquinazolin-2(1H)-ylidene)-3-(2,4-dichlorophenyl)-3-oxo-propanenitrile ["ciliobrevin B"]

2-cyanoethanethioamide (300 mg, 3.00 mmol) and bromoethane (261 μL, 3.50 mmol) were added to an ethanolic solution of sodium ethoxide (3.50 mmol, 2.5 mL). The resulting mixture was stirred for 6 hours, 2-amino-6-chlorobenzoic acid (500 mg, 2.91 mmol) was added, and the reaction was refluxed overnight with stirring. A solid precipitate formed upon cooling of the reaction mixture, which was recovered by vacuum filtration and washed sequentially with ethanol, water, ethanol, and diethyl ether. The solid was then dried to yield 2-(5-chloro-4-oxo-1,4-dihydroquinazolin-2-yl)acetonitrile (148 mg, 22%). $^1$H NMR (400 MHz, DMSO-$d_6$) δ ppm 4.15 (s, 2H), 7.54 (dd, J$_1$=7.8 Hz, J$_2$=1.1 Hz, 1H), 7.61 (dd, J$_1$=8.2 Hz, J$_2$=1.1 Hz, 1H), 7.74 (t, J=8.0 Hz, 1H).

To solution of 2-(5-chloro-4-oxo-1,4-dihydroquinazolin-2-yl)acetonitrile (26.4 mg, 120 μmol) and triethylamine (18.4 μL, 132 μmol) in dioxane (4 mL) was added 2,4-dichlorobenzoyl chloride (18.5 μL, 132 μmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield ciliobrevin B (3) (12.8 mg, 27%). $^1$H NMR (400 MHz, DMSO-$d_6$) δ ppm 7.46 (dd, J$_1$=7.5 Hz, J$_2$=1.4 Hz, 1H), 7.50 (d, J=8.2 Hz, 1H), 7.55 (dd. J$_1$=8.2 Hz, J$_2$=1.9 Hz, 1H), 7.68-7.79 (m, 3H). $^{13}$C NMR (500 MHz, DMSO-$d_6$) δ ppm 71.69, 114.6, 117.63, 118.45, 127.65, 128.1, 129.2, 129.65, 130.49, 133.35, 134.8, 135.47, 138.2, 154.81, 156.48, 188.71. HRMS (m/z): [M+Na]$^+$ calc. for $C_{17}H_8N_3O_2Cl_3Na$, 413.9580; observed, 413.9582.

Example 27

2-(6-chloro-4-oxo-3,4-dihydroquinazolin-2(1H)-ylidene)-3-(2,4-dichlorophenyl)-3-oxopropanenitrile ["ciliobrevin C"]

2-cyanoethanethioamide (501 mg, 5.00 mmol) and bromoethane (448 μL, 6.00 mmol) were added an ethanolic solution of sodium ethoxide (6.00 mmol, 3 mL). The resulting mixture was stirred for 6 hours, 2-amino-5-chlorobenzoic acid (858 mg, 5.00 mmol) was added, and the reaction was refluxed overnight with stirring. A solid precipitate formed upon cooling of the reaction mixture, which was recovered by vacuum filtration and washed sequentially with ethanol, water, ethanol, and diethyl ether. The solid was then dried to yield 2-(6-chloro-4-oxo-1,4-dihydroquinazolin-2-yl)acetonitrile (314 mg, 29%). $^1$H NMR (500 MHz, DMSO-d$_6$) δ ppm 4.18 (s, 2H), 7.70 (d, J=8.8 Hz, 1H), 7.85 (dd, J$_1$=8.7 Hz, J$_2$=2.0 Hz, 1H) 8.03 (d, J=2.4 Hz, 1H).

To solution of 2-(6-chloro-4-oxo-1,4-dihydroquinazolin-2-yl)acetonitrile (52.0 mg, 237 μmol) and triethylamine (36.3 μL, 260 μmol) in dioxane (4 mL) was added 2,4-dichlorobenzoyl chloride (33.1 μL, 237 μmol) and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield ciliobrevin C (4) (6.4 mg, 7%). $^1$H NMR (500 MHz, DMSO-d$_6$) δ ppm 7.50 (d, J$_1$=8.3 Hz, 1H), 7.56 (dd, J$_1$=8.3 Hz, J$_2$=1.9 Hz, 1H), 7.77 (d, J=1.9 Hz, 1H), 7.83 (d, J=8.8 Hz, 1H), 7.88 (dd, J$_1$=8.9 Hz, J$_2$=2.3 Hz, 1H), 8.00 (d, J$_2$=2.4 Hz, 1H). $^{13}$C NMR (500 MHz, DMSO-d$_6$) δ ppm 72.1, 117.52, 118.98, 121.22, 125.61, 127.67, 129.22, 129.66, 129.99, 130.49, 134.88, 135.64, 38.11, 138.58, 155.05, 157.52, 188.76. HRMS (m/z): [M+Na]$^+$ calc. for C$_{17}$H$_8$N$_3$O$_2$Cl$_3$Na, 413.9580; observed, 413.9583.

Example 31

2-(7-chloro-4-oxo-3,4-dihydroquinazolin-2(1H)-ylidene)-3-(2,4-dichlorophenyl)-3-oxo-propanenitrile ["ciliobrevin D"]

2-cyanoethanethioamide (300 mg, 3.00 mmol) and bromoethane (299 μL, 4.00 mmol) were added to an ethanolic solution of sodium ethoxide (4.00 mmol, 3 mL). The resulting mixture was stirred for 6 hours, 2-amino-4-chlorobenzoic acid (500 mg, 2.91 mmol) was added, and the reaction was refluxed overnight with stirring. A solid precipitate formed upon cooling of the reaction mixture, which was recovered by vacuum filtration and washed sequentially with ethanol, water, ethanol, and diethyl ether. The solid was then dried to yield 2-(7-chloro-4-oxo-1,4-dihydroquinazolin-2-yl)acetonitrile (118 mg, 18%). $^1$H NMR (400 MHz, DMSO-d$_6$) δ ppm 4.19 (s, 2H), 7.57 (dd, J$_1$=8.5 Hz, J$_2$=2.1 Hz, 1H), 7.74 (d, J=2.0 Hz, 1H), 8.09 (d, J=8.4 Hz, 1H).

To solution of 2-(7-chloro-4-oxo-1,4-dihydroquinazolin-2-yl)acetonitrile (24.9 mg, 113 μmol) and triethylamine (17.4 μL, 125 μmol) in dioxane (4 mL) was added 2,4-dichlorobenzoyl chloride (15.9 μL, 113 μmol), and the resulting mixture was refluxed overnight with stirring. A solid precipitate formed upon cooling of the reaction mixture, which was recovered by vacuum filtration and washed sequentially with methanol, water, methanol, and dichloromethane. The solid was then dried to yield ciliobrevin D (5) (11.4 mg, 26%). $^1$H NMR (500 MHz, DMSO-d$_6$) δ ppm 7.47-7.52 (m, 2H), 7.56 (dd, J$_1$=8.2 Hz, J$_2$=1.8 Hz, 1H), 7.77 (d, J$_1$=1.8 Hz, 1H), 7.90 (br s, 1H), 8.04 (d, J=8.5 Hz, 1H). $^{13}$C NMR (500 MHz, DMSO-d$_6$) δ ppm 72.44, 116.56, 118.79, 118.85, 125.74, 127.65, 128.66, 129.2, 129.65, 130.49, 134.81, 138.21, 140.03, 155.62, 157.98, 188.6. HRMS (m/z): [M+Na]$^+$ calc. for C$_{17}$H$_8$N$_3$O$_2$Cl$_3$Na, 413.9580; observed, 413.9583.

In like manner the other compounds in the Table 1 below were synthesized.

Assays

Shh-LIGHT2 Assay for Hh Pathway Activity

Shh-N-conditioned medium was prepared as described by Chen et al., Proc. Natl. Acad. Sci. U.S.A. 99, 14071 (2002). Shh-LIGHT2 cells [J. Taipale et al., Nature 406, 1005 (2000)], an NIH-3T3-based cell line containing a stably integrated Gli-responsive firefly luciferase reporter and a constitutive thymidine kinase promoter-driven *Renilla* luciferase expression construct (pRLTK, Promega), were cultured in DMEM containing 10% calf serum. 100 U/mL penicillin, and 0.1 mg/mL streptomycin. The cells were seeded into 96-well plates at a density of 30,000 cells/well, and the following day they were treated with individual compounds or DMSO in DMEM containing 0.5% calf serum, 10% Shh-conditioned medium, and the antibiotics described above. After being cultured for another 24 hours, the cells were lysed and their firefly and *Renilla* luciferase activities were determined using, a dual luciferase reporter kit (Promega) and a microplate luminometer (Veritas). Average values representing the firefly luciferase/*Renilla* luciferase ratio from triplicate samples were used to construct dose response profiles for each compound. Dose-response data from three separate experiments were independently curve-fitted with a variable slope, sigmoidal dose-response algorithm using Prism software, and the resulting IC$_{50}$ values were used to generate an average IC$_{50}$ for each compound.

Quantitative Assessment of Ciliogenesis

Shh-EGFP cells [J. Hyman et al., Proc. Natl. Acad. Sci. U.S.A., (2009)], an NIH-3T3-based cell line containing a stably integrated Gli-responsive enhanced green fluorescent protein reporter, were maintained in DMEM containing 10% calf serum, 100 U/mL penicillin, and 0.1 mg/mL streptomycin. The cells were seeded into 24-well plates containing poly-D-lysine-coated 12-mm glass coverslips at a density of 30,000 cells/well and cultured for 36 hours. The cells were transferred into DMEM containing 0.5% calf serum, the antibiotics described above, and either individual compounds at a 30 μM concentration or 0.3% DMSO. After being cultured for another 24 hours, the cells were fixed in PBS containing 4% paraformaldehyde for 10 minutes at room temperature, washed 3×5 minutes with PBS, permeabilized with PBS containing 0.3% Triton X-100 for 5 minutes, and blocked overnight at 4° C. with PBS containing 5% normal goat serum, 0.1% Triton X-100, and 0.05% sodium azide. The coverslips were then incubated for 90 minutes at room temperature with blocking buffer containing rabbit polyclonal anti-Arl 13b antibody (1:3000 dilution), washed 4×5 minutes with PBS containing 0.1% Triton X-100, and incubated for 60 minutes with blocking buffer containing Alexa Fluor 488-conjugated goat polyclonal anti-rabbit IgG antibody (1:300 dilution; Invitrogen, A-11034). Following this secondary antibody incubation, nuclei were stained by incubating the cells 2×10 minutes with PBS containing 0.1% Triton X-100 and 0.51 Ag/mL 4',6-diamidino-2-phenylindole (DAPI) and washing them 2×5 minutes with PBS. The coverslips were subsequently mounted onto slides using Prolong Gold Antifade Reagent (Invitrogen) and imaged using an HC Plan Apochromat CS 20×/0.70 NA oil immersion objective on a Leica DMI6000B compound microscope equipped with a Photometric CoolSNAP HQ CCD camera and Metamorph software (Molecular Devices). Images of Arl13b staining in DMSO-treated cells were manually examined to establish a minimum threshold value for cilia staining intensity. ImageJ software was then used to define objects consisting of two or more adjacent pixels with a signal intensity equal to or greater than this threshold value, and the total object area within an individual image was used to estimate the total pixel area of primary cilia. Corresponding images of DAPI staining were processed in parallel using CellProfiler software to establish the number of nuclei per image. The average cilia size per cell within an individual image was then determined by dividing the total ciliary pixel area by the number of nuclei. Ten individual images, each containing approximately 150 cells, were used to quantify the average cilia size for each experimental condition.

Representative results of these studies are outlined in Table 1.

TABLE 1

| Example number | Structure | IC$_{50}$ in Shh-LIGHT2 assay | Primary cilia size (percent of DMSO control at a 30 µM dose) |
|---|---|---|---|
| 1 | 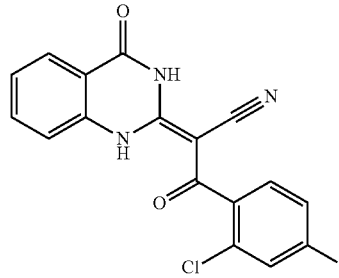 | 9.9 µM | 27 |
| 2 | 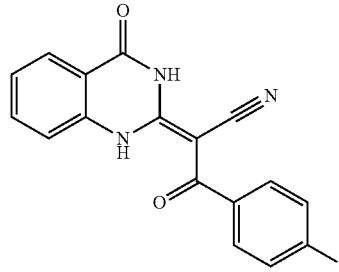 | 5.2 µM | 74 |
| 3 | 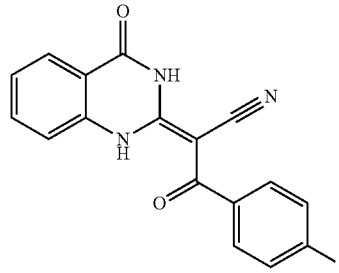 | 5 µM | |
| 4 | 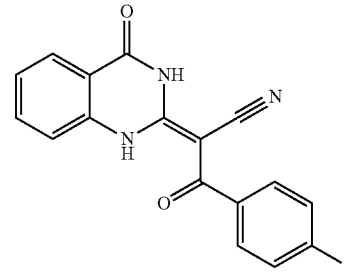 | 4.5 µM | |

TABLE 1-continued

| Example number | Structure | IC$_{50}$ in Shh-LIGHT2 assay | Primary cilia size (percent of DMSO control at a 30 μM dose) |
| --- | --- | --- | --- |
| 5 | (quinazolinone with 4-methylphenyl ketone cyanoacrylate) | 15 μM | |
| 6 | (quinazolinone with 4-i-Bu phenyl ketone cyanoacrylate) | 6.5 μM | |
| 7 | (quinazolinone with 4-n-pentyl phenyl ketone cyanoacrylate) | 5.5 μM | |
| 8 | (quinazolinone with 4-OMe phenyl ketone cyanoacrylate) | 30 μM | |
| 9 | (quinazolinone with 4-NO$_2$ phenyl ketone cyanoacrylate) | 25 μM | |

TABLE 1-continued

| Example number | Structure | IC$_{50}$ in Shh-LIGHT2 assay | Primary cilia size (percent of DMSO control at a 30 μM dose) |
|---|---|---|---|
| 10 | (2-Cl phenyl derivative) | 25 μM | 93 |
| 11 | (2-F phenyl derivative) | 30 μM | |
| 12 | (2-Br phenyl derivative) | 15 μM | |
| 13 | (2-I phenyl derivative) | 20 μM | |
| 14 | (2-CH$_3$ phenyl derivative) | 30 μM | |

TABLE 1-continued

| Example number | Structure | IC$_{50}$ in Shh-LIGHT2 assay | Primary cilia size (percent of DMSO control at a 30 μM dose) |
|---|---|---|---|
| 15 | 2-[(4-oxo-1,4-dihydroquinazolin-2(3H)-ylidene)]-3-(2-methoxyphenyl)-3-oxopropanenitrile | >30 μM | |
| 16 | 2-[(4-oxo-1,4-dihydroquinazolin-2(3H)-ylidene)]-3-oxo-3-phenylpropanenitrile | 23 μM | 95 |
| 17 | 2-[(4-oxo-1,4-dihydroquinazolin-2(3H)-ylidene)]-3-(3-chlorophenyl)-3-oxopropanenitrile | 5.5 μM | 68 |
| 18 | 2-[(4-oxo-1,4-dihydroquinazolin-2(3H)-ylidene)]-3-(3,4-dichlorophenyl)-3-oxopropanenitrile | 3 μM | 16 |

TABLE 1-continued

| Example number | Structure | IC$_{50}$ in Shh-LIGHT2 assay | Primary cilia size (percent of DMSO control at a 30 μM dose) |
| --- | --- | --- | --- |
| 19 | 3,5-dichlorophenyl derivative | 3 μM | 65 |
| 20 | 3,4,5-trimethoxyphenyl derivative | >30 μM | |
| 21 | 1-naphthyl derivative | 20 μM | |
| 22 | 3-methylphenyl derivative | 5 μM | |

TABLE 1-continued

| Example number | Structure | IC$_{50}$ in Shh-LIGHT2 assay | Primary cilia size (percent of DMSO control at a 30 μM dose) |
| --- | --- | --- | --- |
| 23 | (structure) | 4.4 μM | 70 |
| 24 | (structure) | >50 μM | 104 |
| 25 | (structure) | 11 μM | 32 |
| 26 | (structure) | 10 μM | |
| 27 | (structure) | 6.1 μM | 11 |

TABLE 1-continued

| Example number | Structure | IC$_{50}$ in Shh-LIGHT2 assay | Primary cilia size (percent of DMSO control at a 30 μM dose) |
| --- | --- | --- | --- |
| 28 | 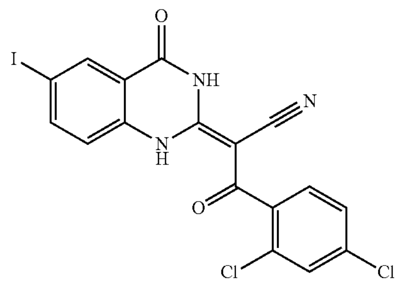 [SMILES: N#C/C(C(=O)c1ccc(Cl)cc1Cl)=C1\NC(=O)c2cc(I)ccc2N1] | 6 μM | |
| 29 | 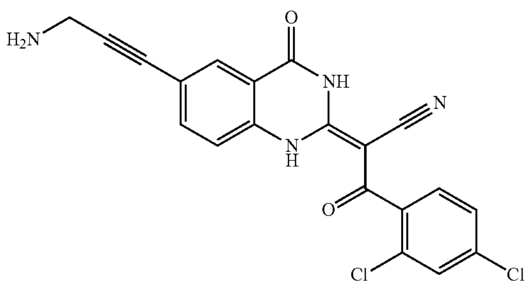 [SMILES: N#C/C(C(=O)c1ccc(Cl)cc1Cl)=C1\NC(=O)c2cc(C#CCN)ccc2N1] | 20 μM | |
| 30 | 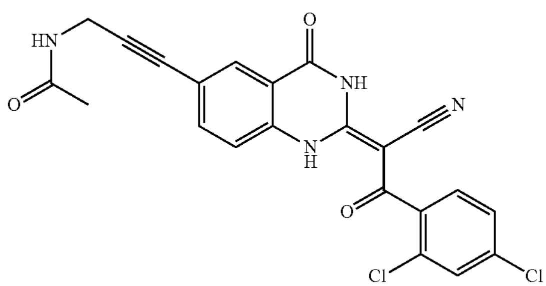 [SMILES: CC(=O)NCC#Cc1ccc2c(c1)C(=O)N/C(=C(\C#N)C(=O)c1ccc(Cl)cc1Cl)N2] | 30 μM | |
| 31 | 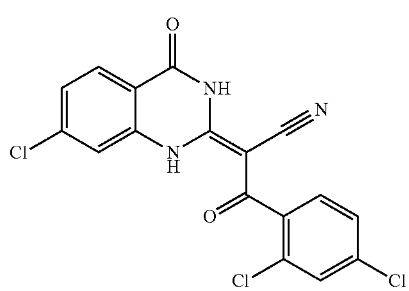 [SMILES: N#C/C(C(=O)c1ccc(Cl)cc1Cl)=C1\NC(=O)c2ccc(Cl)cc2N1] | 15 μM | 7 |
| 32 | 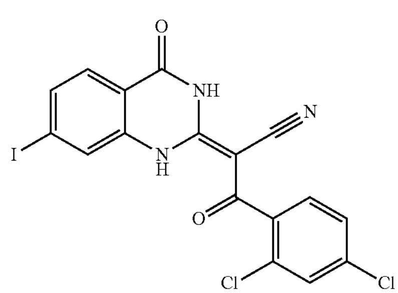 [SMILES: N#C/C(C(=O)c1ccc(Cl)cc1Cl)=C1\NC(=O)c2ccc(I)cc2N1] | 12 μM | |

TABLE 1-continued

| Example number | Structure | IC$_{50}$ in Shh-LIGHT2 assay | Primary cilia size (percent of DMSO control at a 30 μM dose) |
|---|---|---|---|
| 33 | (structure: 7-methoxy-quinazolinone with cyanoacetyl-2,4-dichlorophenyl substituent) | 15 μM | |

Hh signaling is primarily mediated by the transcription factors Gli2 and Gli3, and under basal conditions these proteins are partially proteolyzed to generate N-terminal repressors (Gli2/3R) in a proteosome- and cilium-dependent manner. The binding of Hh ligands to the transmembrane receptor Patched1 (Ptch1) leads to Smo activation and inhibition of Gli proteolytic processing; full-length Gli2 and Gli3 (Gli2/3FL) then dissociate from Sufu and are converted into transcriptional activators (Gli2/3A). Like Gli2/3 processing, Gli2/3A formation requires the primary cilium.

Quantitative Assessment of Hh Ligand-Dependent Gli3 Processing

Shh-EGFP cells were seeded into 12-well plate at a density of 120,000 cells/well in DMEM containing 10% calf serum. 100 U/mL penicillin, and 0.1 mg/mL streptomycin. After being cultured for 24 hours, the cells were transferred into DMEM containing 0.5% calf serum, 10% Shh-conditioned medium, the antibiotics described above, and either individual compounds or DMSO. The cells were cultured for an additional 16 hours, washed with PBS, and then lysed by incubation on ice with SDS-PAGE loading buffer composed of 8% glycerol, 20 mM Tris-HCl, pH 6.8, 2% SDS, 100 mM DTT, 1 mM PMSF, 20 mM NaF, 2 mM Na$_3$VO$_4$, and an EDTA-free protease inhibitor cocktail (Roche). The lysed samples were heated to 100° C. for 7 minutes, loaded onto 3-8% Criterion XT Tris-Acetate polyacrylamide gels (Bio-Rad), electrophoresed in XT Tricine buffer (Bio-Rad), and transferred onto PVDF membranes. The membranes were dehydrated with methanol and probed overnight at 4° C. with goat polyclonal anti-Gli3 antibody (0.4 μg/mL: R & D Systems, AF3690) in PBS containing 4% non-fat dry milk and 0.1% Tween-20 (immunoblot blocking buffer). The blots were then washed 4×1 minutes in PBS and incubated with horseradish peroxidase-conjugated bovine polyclonal anti-goat IgG antibody (0.04 μg/mL, Jackson ImmunoResearch, 805-035-180) in immunoblot blocking buffer for 1 hour at room temperature. The membranes were next washed 4×1 minutes in PBS and visualized using SuperSignal West Dura Extended Duration substrate (Thermo Scientific) and a ChemiDoc XRS imaging system (Bio-Rad). Band intensities of Gli3FL and Gli3R where quantified using Quantity One software (Bio-Rad), and five independent experiments were used to determine the average Gli3FL/Gli3R ratio for each compound. The ciliobrevins (compounds of examples 1, 25, 27 and 31) altered the Gli3FL/Gli3R ratio in cells stimulated with the N-terminal domain of Sonic Hedgehog (Shh-N) in a manner reminiscent of the Smo inhibitor cyclopamine. Shh-N-dependent Gli3FL phosphorylation was also reduced by these compounds, perhaps reflecting loss of Gli3A. Other analogs tested did not exhibit a significant effect on the Gli3FL/Gli3R ratio or Gli3FL phosphorylation state.

Quantitative Assessment of Hh Ligand-Dependent Gli2 Trafficking

The forgoing pharmacological results are concordant with genetic studies that have established a link between primary cilia function, Gli processing, and Gli activation. Since Hh pathway activation coincides with Gli2 accumulation at the distal tip of the primary cilium, we examined the effect of test compounds on Gli2 localization to gain a better understanding of how the ciliobrevins perturb the cilium.

Shh-EGFP cells were seeded into 24-well plates containing poly-D-lysine-coated 12-mm glass coverslips at a density of 65,000 cells/well and cultured for 24 hours in DMEM containing 10% calf serum, 100 U/mL penicillin, and 0.1 mg/mL streptomycin. The cells were then transferred into DMEM containing 0.5% calf serum and the antibiotics described above for 16 hours to promote primary cilia formation. The cells were next transferred into DMEM containing 0.5% calf serum, antibiotics, and either individual compounds at a 30 μM concentration or 0.3% DMSO. Each compound or vehicle treatment was conducted in the presence or absence of 10% Shh-N-conditioned medium, and the cells were cultured under these conditions for 4 hours. The cells were subsequently fixed in PBS containing 4% paraformaldehyde for 10 minutes at room temperature, washed 3×5 minutes in PBS containing 50 mM glycine, permeabilized in PBS containing 0.3% Triton X-100 for minutes, and then blocked overnight at 4° C. in PBS containing 5% normal donkey serum, 0.1% Triton X-100, and 0.05% sodium azide. After blocking was complete, the coverslips were incubated in blocking buffer containing rabbit polyclonal anti-Arl13b antibody (1:3000 dilution), goat polyclonal anti-Gli2 antibody (1:50 dilution; R & D Systems, AF3635), and mouse monoclonal anti-γ-tubulin (1:200 dilution; Sigma-Aldrich, T5326) for 90 minutes at room temperature. The cells were then washed 4×5 minutes with PBS containing 0.1% Triton X-100 and incubated in blocking buffer containing DyLight 488-conjugated donkey polyclonal anti-goat IgG antibody (3 μg/mL; Jackson ImmunoResearch, 705-485-147), DyLight 594-conjugated donkey polyclonal anti-mouse IgG antibody (3 μg/mL; Jackson ImmunoResearch, 715-515-151), and DyLight 649-conjugated donkey polyclonal anti-mouse IgG antibody (3 μg/mL; Jackson ImmunoResearch, 711-495-152) for 60 minutes. Following, this secondary antibody incubation, nuclei were stained by incubating the cells 2×10 minutes with PBS containing 0.1% Triton X-100 and 0.5 µg/mL DAPI and washing them 2×5 minutes with PBS. The coverslips were subsequently mounted onto slides using Prolong Gold Antifade Reagent (Invitrogen) and imaged using a Plan Apochromat 63×/1.4 NA oil immersion objective on a Zeiss Axio1mager Z1 upright microscope equipped with an LSM700 laser scanning confocal head. Ciliary Gli2 levels were quantified by determining total pixel intensity within a 0.69 µm-diameter circle at the distal tip of the axoneme and subtracting background fluorescence in an adjacent region of equivalent size. At least 25 cilia were analyzed to determine the average ciliary Gli2 level for each experimental condition. Basal and Shh-N-induced levels of ciliary Gli2 were unchanged by derivatives that do not significantly perturb ciliogenesis (16 and 2), whereas compounds 1 and 31 increased basal Gli2 concentrations in this signaling organelle to levels comparable to that induced by Shh-N.

Quantitative Assessment of IFT88 Trafficking

The ability of ciliobrevins to increase ciliary Gli2 levels in a Hh ligand-independent manner suggests that these compounds might target protein trafficking mechanisms within the primary cilium. As a microtubule-based compartment, the cilium utilizes specific motor proteins to move macromolecules along its axoneme. Intraflagellar transport (IFT) of cargo can be resolved into anterograde trafficking, which requires the plus end-directed kinesin-2 motor and the IFTB multisubunit complex, and retrograde trafficking, which utilizes the minus end-directed cytoplasmic dynein 2 motor and the IFTA complex. The genetic disruption of individual kinesin-2, cytoplasmic dynein 2, or IFT complex subunits has been previously found to induce ciliary defects and perturb Hh signaling. For example, loss of a primary cilia-specific cytoplasmic dynein 2 heavy chain (Dync2hl) has been shown to alter cilial morphology and to reduce Hh target gene expression in mouse embryos. Cells lacking Dync2hl function also exhibit increased levels of ciliary Gli2 in the absence of Hh pathway activation. To confirm that ciliobrevins target cilia trafficking in general rather than a Hh pathway-specific process, we examined the effect of ciliobrevins on the subcellular localization of IFTB component IFT88, which requires cytoplasmic dynein 2-dependent retrograde transport for its return to the ciliary basal body.

Shh-EGFP cells were seeded into 24-well plates containing poly-D-lysine-coated 12-mm glass coverslips at a density of 30,000 cells/well and cultured for 24 hours in DMEM containing 10% calf serum, 100 U/mL penicillin, and 0.1 mg/mL streptomycin. The cells were then transferred into DMEM containing 0.5% calf serum and the antibiotics described above for 16 hours to promote primary cilia formation. The cells were next transferred into DMEM containing 0.5% calf serum, antibiotics, and either individual compounds at a 50 µM concentration or 0.25% DMSO for 1 h. The cells were subsequently fixed in PBS containing 4% paraformaldehyde for 10 minutes at room temperature, washed 3×5 minutes in PBS containing 50 mM glycine, permeabilized in PBS containing 0.3% Triton X-100 for 5 minutes, and then blocked overnight at 4° C. in PBS containing 5% normal goat serum. 0.1% Triton X-100, and 0.05% sodium azide. After blocking was complete, the coverslips were incubated in blocking buffer containing mouse monoclonal anti-acetylated-tubulin (1:4000 dilution; Sigma-Aldrich, T6793), rabbit polyclonal anti-IFT88 antibody (1:70 dilution; ProteinTech Group, 13967-1-AP), and mouse monoclonal anti-γ-tubulin (1:200 dilution; Sigma-Aldrich, T5326) for 90 minutes at room temperature. The cells were then washed 4×5 minutes with PBS containing 0.1% Triton X-100 and incubated in blocking buffer containing Alexa Fluor 488-conjugated goat polyclonal anti-rabbit IgG antibody (1:300 dilution; Invitrogen, A-11034) and Alexa Fluor 647-conjugated goat polyclonal anti-mouse IgG antibody (1:300 dilution; Invitrogen, A-21235). Following this secondary antibody incubation, nuclei were stained by incubating the cells 2×10 minutes with PBS containing 0.1% Triton X-100 and 0.5 µg/mL DAPI and washing them 2×5 minutes with PBS. The coverslips were subsequently mounted onto slides using Prolong Gold Antifade Reagent (Invitrogen) and imaged using a Plan Apochromat 63×/1.4 NA oil immersion objective on a Zeiss Axio1mager Z1 upright microscope equipped with an LSM700 laser scanning confocal head. Ciliary IFT levels were quantified essentially as described for Gli2 though no background was subtracted. At least 25 cilia were analyzed to determine the average ciliary IFT88 level for each experimental condition. Treating cells for one hour with ciliobrevin D (example 31) caused a significant increase in IFT88 levels at the distal tip of primary cilia as compared to DMSO or to compound 16, providing further evidence that the ciliobrevins inhibit cytoplasmic dynein 2 function.

Imaging of Mitotic Spindle Assembly

In addition to trafficking macromolecules out of the primary cilium, cytoplasmic dynein complexes have other cellular functions. For example, cytoplasmic dynein 1 acts in concert with dynactin and the nuclear protein NuMA to crosslink and focus the minus ends of microtubules within the mitotic spindle. These actions create the canonical fusiform shape and localize γ-tubulin-containing, microtubule-nucleating complexes to the spindle poles. Cytoplasmic dynein 1 inhibition by blocking antibodies or dominant negative constructs disrupts mitotic spindle assembly, resulting in splayed microtubule ends and reduced γ-tubulin recruitment. To determine whether ciliobrevins can recapitulate these phenotypes, we treated a metaphase-enriched population of NIH-3T3 cells with 50 µM of either example 31 or example 2 for one hour and examined their mitotic structures by confocal immunofluorescence microscopy.

Shh-EGFP cells were cultured until they achieved approximately 70% confluency and then split 1:5 into 24-well plates containing, poly-D-lysine-coated 12-mm glass coverslips in DMEM containing 10% calf serum, 100 U/mL penicillin, and 0.1 mg/mL streptomycin. After culturing under these conditions overnight, the cells were transferred into growth medium containing 15 µM MG132 for 90 minutes, followed by a 60-minute incubation with DMEM containing 0.5% calf serum, 15 µM MG132, and either individual compounds at a 50 µM dose or an equivalent amount of the DMSO vehicle. The cells were fixed by incubation on ice with methanol chilled to −20° C., washed 3×5 minutes in PBS, and then blocked for 1 hour at room temperature with PBS containing 5% normal goat serum, 0.1% Triton X-100, and 0.05 sodium azide. After blocking was complete, the coverslips were incubated in blocking buffer containing mouse monoclonal anti-α-tubulin antibody (1:2000 dilution; Sigma-Aldrich, T6199) and rabbit polyclonal anti-γ-tubulin antibody (1:500 dilution; Sigma-Aldrich, T3559) for 90 minutes at room temperature. The cells were then washed 4×5 minutes with PBS containing 0.1% Triton X-100 and incubated in blocking buffer containing Alexa Fluor 488-conjugated goat polyclonal anti-rabbit IgG antibody (1:300 dilution; Invitrogen, A-11034) and Alexa Fluor 594-conjugated goat polyclonal anti-mouse IgG antibody (1:300 dilution:Invitrogen, A-11032) for 60 minutes.

Following this secondary antibody incubation, nuclei were stained by incubating the cells 2×10 minutes with PBS containing 0.1% Triton X-100 and 0.5 µg/mL DAPI and washing them 2×5 minutes with PBS. The coverslips were subsequently mounted onto slides using Prolong Gold Antifade Reagent (Invitrogen) and imaged using a Plan Apochromat 63×/1.4 NA oil immersion objective on a Zeiss Axio1mager Z1 upright microscope equipped with an LSM700 laser scanning confocal head. Consistent with the pharmacological inhibition of cytoplasmic dynein 1, cells treated with example 31 failed to achieve mitotic spindles with focused γ-tubulin-positive poles. Cells treated with example 16 or vehicle alone exhibited normal spindle morphologies.

Melanosome Aggregation Assay

Another cytoplasmic dynein 1-dependent process is the aggregation of melanin-containing vesicles in pigment cells, the mechanism by which certain organisms adapt their coloration in response to environmental cues. For example, cytoplasmic dynein 1 transports melanosomes toward the center of *Xenopus* melanophores stimulated with the small-molecule melatonin, counterbalancing the kinesin-2- and myosin-V-driven dispersal of these pigment granules toward the cell periphery in response to melanocyte-stimulating hormone (MSH). To determine if melanosome trafficking is sensitive to the ciliobrevins, we cultured *Xenopus* melanophores with MSH to uniformly disperse their melanosomes and then treated them with melatonin and various concentrations of test compounds.

Immortalized *Xenopus* melanophores were cultured in 0.7×L15 medium supplemented with 10% fetal bovine serum, 30 mg/L L-glutamine, and 5 mg/L insulin. The cell were cultured on poly-D-lysine-coated coverslips in 12-well plates for 12 to 24 hours prior to the melanosome aggregation assay. On the day of the experiment, the melanophores were cultured in serum-free medium for 30 minutes, stimulated with 100 nM melanocyte-stimulating hormone (MSH) to uniformly disperse the melanosomes, and then incubated with medium containing individual compounds or DMSO for 10 minutes. Melanosome aggregation was then induced by treating the cells with 10 nM melatonin in the presence of the test compound. The melanophores were either imaged immediately by time-lapse microscopy or fixed after 30 minutes with 0.7×PBS containing 4% paraformaldehyde.

To demonstrate the reversibility of the ciliobrevins, the melanophores were cultured in serum-free medium for 30 minutes, stimulated with 100 nM melanocyte-stimulating hormone (MSH) to uniformly disperse the melanosomes, and then incubated with medium containing individual compounds and 10 nM melatonin for 30 minutes. The cells were then washed several times with medium containing melatonin alone and imaged. While example 31 significantly inhibited melanosome aggregation at a 10 μM dose, example 16, which did not disrupt cilia, had no discernible effect at concentrations up to 40 μM. The effects of ciliobrevin D (example 31) were completely reversible, as demonstrated by washout experiments in which the melanophores were initially treated with example 31 and melatonin and then cultured in medium containing melatonin alone. Taken all together, these results indicate that the ciliobrevins are specific, reversible inhibitors of disparate cytoplasmic dynein-dependent processes, including ciliogenesis, ciliary trafficking, mitotic spindle assembly, and melanosome transport.

Microtubule Surface Gliding Assay

The diverse cellular contexts in which the ciliobrevins act strongly suggests that they target cytoplasmic dynein itself rather than upstream signaling events that converge on this multisubunit motor protein. To more directly examine whether cytoplasmic dynein is the direct target of the ciliobrevins, we evaluated their effects on dynein-dependent microtubule gliding in vitro. Cytoplasmic dynein was purified from bovine brain tissue, adsorbed onto glass slides, and then incubated with fluorescently labeled microtubules and ATP in the presence or absence of these compounds. We then imaged and quantified the resulting microtubule gliding velocities by epifluorescence microscopy.

Cytoplasmic dynein was purified from bovine brains as described by Bingham et al. [Methods Enzymol. 298, 171 (1998)]. K560, a 560-amino acid N-terminal fragment of human conventional kinesin (kinesin-1) with a C-terminal His-tag, was expressed in bacteria and purified as described by Woehlke et al., [*Cell* 90, 207 (1997)]. Motility assays were performed on a Zeiss Axiovert 200M wide-field microscope equipped with a Zeiss 100×/1.45 NA α-Plan-Fluar objective. Data were captured with an EM-CCD camera (iXon DU-897, Andor Technology) with a 0.3-second exposure time and frame rate of 0.5 second$^{-1}$. Microtubule gliding assays were performed as described by Kapoor and Mitchison [Proc. Natl. Acad. Sci. U.S.A. 96, 9106 (1999)] with some modifications. An approximately 6 μL flow chamber was filled with motor protein (100 μg/mL dynein or 50 μg/mL K560) in motor dilution buffer (80 mM Pipes, 1 mM EGTA, 2 mM $MgCl_2$, 2 mM DTT, 50 μM ATP, pH 6.8 with KOH). After a 2-minute incubation, excess protein was washed out with 20 μL of PEM80 buffer (80 mM Pipes, 1 mM EGTA, 2 mM $MgCl_2$, pH 6.8 with KOH) and the surface was blocked against non-specific microtubule binding by filling the chamber with blocking protein (0.5 mg/mL α-casein for dynein experiments and 1 mg/mL BSA for K560 experiments) in motor dilution buffer. After 2 minutes the chamber was perfused with 18 μL of reaction mix (PEM80, 40 mM KCl, blocking protein [1 mg/mL a-casein for dynein experiments; 1 mg/mL BSA for K560 experiments], 2 mM MgATP, 20 μM taxol, 0.1 μM rhodamine-labeled microtubules, oxygen depletion system [4 mM DTT, 2 mM glucose, 40 μg/mL glucose oxidase, 35 μg/mL catalase], 2.5% DMSO, and test compounds as appropriate). The flow chamber was then sealed with valap. After allowing the microtubules to bind to the surface for 5 minutes, the gliding microtubules were visualized by time-lapse fluorescence microscopy. Velocities were measured by kymography using Metamorph software (Molecular Devices), and the velocity for each microtubule was determined from the total distance during the time observed.

For washout experiments, the chamber was left unsealed after the initial reaction mix containing inhibitor was added. Microtubules were allowed to bind to the surface for 5 minutes, and then a time-lapse movie was acquired. The inhibitor was then washed out of the chamber by flowing in 20 μL of fresh reaction mix (PEM80, 40 mM KCl, 1 mg/mL α-casein, 2 mM MgATP, 20 μM taxol, oxygen depletion system, and 2.5% DMSO) without additional microtubules or inhibitor. The chamber was sealed, and additional time-lapse movies were acquired.

All compounds were initially tested at 100 μM concentrations, with ciliobrevins A and D (examples 1 and 31) retarding microtubule movement by at least five-fold in this assay; analogs that did not perturb cytoplasmic dynein-dependent processes in our cell-based assays (examples 2 and 16), had minimal effects. As with melanosome aggregation in *Xenopus* pigment cells, microtubule gliding inhibition by the ciliobrevins was reversible and dose-dependent, with the two compounds exhibiting $IC_{50}$ values of 30 μM and 40 μM, respectively. Neither ciliobrevin significantly affected K560/kinesin-1-dependent microtubule gliding in vitro at 100 μM concentrations. Thus, these dihydroquinazolinones specifically target cytoplasmic dynein and are not general antagonists of ATP-dependent microtubule motility.

Quantitative Assessment of Ciliogenesis

Shh-EGFP cells, an NIH-3T3-based cell line containing a stably integrated Gli-responsive enhanced green fluorescent protein reporter, were maintained in DMEM containing 10% (v/v) calf serum, 100 U/mL penicillin, and 0.1 mg/mL streptomycin. The cells were seeded into 24-well plates containing poly-D-lysine-coated 12-mm glass coverslips at a density of 30,000 cells/well and cultured for 36 hours. The cells were transferred into DMEM containing 0.5% (v/v) calf serum, the antibiotics described above, and either individual dihydroquinazolinones at a 30 µM concentration or an equivalent amount of DMSO vehicle (0.3%, v/v). After being cultured for another 24 hours, the cells were fixed in PBS containing 4% (w/v) paraformaldehyde for 10 min at room temperature, washed 3×5 min with PBS, permeabilized with PBS containing 0.3% (v/v) Triton X-100 for 5 min, and blocked overnight at 4° C. with PBS containing 5% (v/v) normal goat serum, 0.1% (v/v) Triton X-100, and 0.05% (w/v) sodium azide. The coverslips were then incubated for 90 min at room temperature with blocking buffer containing rabbit polyclonal anti-Arl13b antibody (1:3000 dilution), washed 4×5 min with PBS containing 0.1% Triton (v/v) X-100, and incubated for 60 min with blocking buffer containing Alexa Fluor 488-conjugated goat polyclonal anti-rabbit IgG antibody (1:300 dilution; Invitrogen, A-11034). Following this secondary antibody incubation, nuclei were stained by incubating the cells 2×10 min with PBS containing 0.1% (v/v) Triton X-100 and 0.5 µg/mL 4',6-diamidino-2-phenylindole (DAPI) and washing them 2×5 min with PBS. The coverslips were subsequently mounted onto slides using Prolong Gold Antifade Reagent (Invitrogen) and imaged using an HC Plan Apochromat CS 20×/0.70 NA oil immersion objective on a Leica DMI6000B compound microscope equipped with a Photometric CoolSNAP HQ CCD camera and Metamorph software (Molecular Devices). Images of Arl13b staining in DMSO-treated cells were manually examined to establish a minimum threshold value for cilia staining intensity. ImageJ software was then used to define objects consisting of two or more adjacent pixels with a signal intensity equal to or greater than this threshold value, and the total object area within an individual image was used to estimate the total pixel area of primary cilia. Corresponding images of DAPI staining were processed in parallel using CellProfiler software to establish the number of nuclei per image. The average cilia size per cell within an individual image was then determined by dividing the total ciliary pixel area by the number of nuclei. Ten individual images, each containing approximately 150 cells, were used to quantify the average cilia size for each experimental condition. The results are shown in FIG. 1. There was a dose-dependent decrease in cilia size in response to increasing concentration of the compound of example 1, whereas the compound of example 16, which is an inhibitor of hedgehog signaling, but not an inhibitor of dynein, exhibits no decrease in cilia size in response to increasing concentration.

Compounds disclosed herein are therefore the first small molecules known to specifically inhibit cytoplasmic dynein in vitro and in live cells. Although the ATP analog erythro-9 [-3-(2-hydroxynonyl)]adenine and the antioxidant nordihydroguaiaretic acid have been previously reported to abrogate dynein function, these compounds are promiscuous enzyme antagonists. The natural product purealin can partially inhibit the ATPase activity of a dynein motor domain in vitro, but its ability to block cytoplasmic dynein-dependent cellular processes has not been demonstrated. The studies described above indicate that the ciliobrevins can inhibit both cytoplasmic dynein 1 and 2, and accordingly, the compounds will be broadly applicable probes of dynein-dependent processes, complementing other small-molecule modulators of motor proteins such as the Eg5 inhibitor monastrol and the myosin II antagonist blebbistatin.

The invention claimed is:

1. A compound of formula

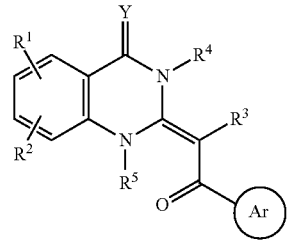

wherein $R^1$ is chosen from —$(C_3-C_{10})$hydrocarbon, —O—$(C_3-C_6)$ alkyl, and -A-$R^{10}$, wherein A is a $(C_1-C_6)$hydrocarbon and $R^{10}$ is chosen from —O—$(C_1-C_6)$alkyl, fluoro$(C_1-C_6)$alkyl, —O—$(C_1-C_6)$fluoroalkyl, hydroxy, —CN, nitro, —S—$(C_1-C_6)$alkyl, $(C_1-C_6)$alkoxycarbonyl, $(C_1-C_6)$acyl, amino, $(C_1-C_6)$alkylamino, di$(C_1-C_6)$alkylamino and $(C_1-C_6)$acylamino; and $R^2$ is hydrogen;

$R^3$ is chosen from cyano, nitro, acetyl and —C(=O)NH$_2$;

$R^4$ and $R^5$ are independently chosen from hydrogen and methyl;

Y is O;

and

Ar is chosen from;

a. phenyl substituted with from one to three substituents independently chosen from halogen, $(C_1-C_{10})$hydrocarbon, fluoro$(C_1-C_6)$alkyl, —O$(C_1-C_6)$fluoroalkyl, —CN, nitro, $(C_1-C_6)$alkoxycarbonyl and $(C_1-C_6)$acyl; and b. naphthyl, and thiophenyl, either of which may be optionally substituted with from one to three substituents independently chosen from halogen, $(C_1-C_{10})$ hydrocarbon, fluoro$(C_1-C_6)$alkyl, —O$(C_1-C_6)$fluoroalkyl, —CN, nitro, $(C_1-C_6)$alkoxycarbonyl and $(C_1-C_6)$acyl.

2. A compound according to claim 1 wherein Ar is chosen from substituted phenyl and naphthyl, and thiophenyl, any of which may be optionally substituted with from one to three substituents independently chosen from halogen, $(C_1-C_{10})$ hydrocarbon, fluoro$(C_1-C_6)$alkyl, —O—$(C_1-C_6)$fluoroalkyl, —CN, nitro, $(C_1-C_6)$alkoxycarbonyl and $(C_1-C_6)$acyl.

3. A compound according to claim 2 wherein Ar is phenyl substituted with from one to three halogens.

4. A compound according to claim 3 wherein Ar is 2,4-dichlorophenyl or 3,4-dichlorophenyl.

5. A compound according to claim 1 wherein $R^4$ and $R^5$ are hydrogen.

6. A compound according to claim 1 wherein $R^3$ is CN.

7. A compound according to claim 4 wherein $R^3$ is CN; and $R^2$, $R^4$ and $R^5$ are H.

8. A method of inhibiting a dynein comprising bringing said dynein into contact with a compound of formula

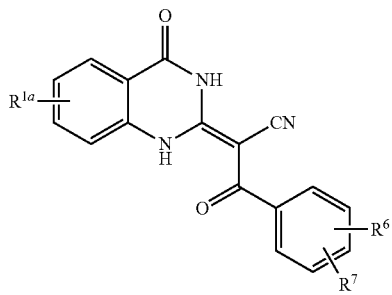

wherein
$R^{1a}$ is —$(C_3$-$C_{10})$hydrocarbon, or —O—$(C_3$-$C_6)$alkyl; and $R^6$ and $R^7$ are halogen.

9. A method of inhibiting retrograde cilial transport comprising bringing a cell having at least one *cilium* into contact with a compound of formula

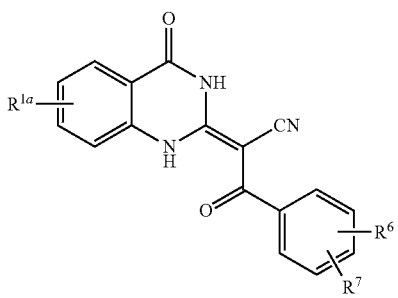

wherein
$R^{1a}$ is —$(C_3$-$C_{10})$hydrocarbon, or —O—$(C_3$-$C_6)$alkyl; and $R^6$ and $R^7$ are halogen.

10. A method according to claim 9 wherein said method of inhibiting is an in vitro method.

11. A method according to claim 9 wherein said method of inhibiting is an in vivo method.

12. A method of inhibiting the growth of a basal cell carcinoma, glioblastoma or medulloblastoma comprising bringing said basal cell carcinoma, glioblastoma or medulloblastoma into contact with a compound of formula

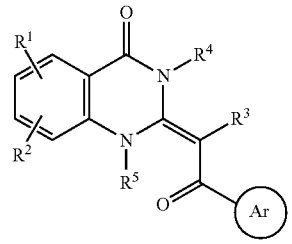

wherein
$R^1$ is chosen from —$(C_3$-$C_{10})$hydrocarbon, —O—$(C_3$-$C_6)$alkyl, and -A-$R^{10}$, wherein A is a $(C_1$-$C_6)$hydrocarbon and $R^{10}$ is chosen from —O—$(C_1$-$C_6)$alkyl, fluoro$(C_1$-$C_6)$alkyl, —O—$(C_1$-$C_6)$fluoroalkyl, hydroxy, —CN, nitro, —S—$(C_1$-$C_6)$alkyl, $(C_1$-$C_6)$alkoxycarbonyl, $(C_1$-$C_6)$acyl, amino, $(C_1$-$C_6)$alkylamino, di$(C_1$-$C_6)$alkylamino and $(C_1$-$C_6)$acylamino; and $R^2$ is hydrogen;

$R^3$ is chosen from hydrogen, cyano, nitro, acetyl and —C(=O)NH$_2$;

$R^4$ and $R^5$ are independently chosen from hydrogen and methyl;

Y is O;

and

Ar is chosen from:
  a. phenyl substituted with from one to three substituents independently chosen from halogen, $(C_1$-$C_{10})$hydrocarbon, fluoro$(C_1$-$C_6)$alkyl, —O$(C_1$-$C_6)$fluoroalkyl, —CN, nitro, $(C_1$-$C_6)$alkoxycarbonyl and $(C_1$-$C_6)$ acyl; and
  b. naphthyl, and thiophenyl, either of which may be optionally substituted with from one to three substituents independently chosen from halogen, $(C_1$-$C_{10})$ hydrocarbon, fluoro$(C_1$-$C_6)$alkyl, —O$(C_1$-$C_6)$fluoroalkyl, —CN, nitro, $(C_1$-$C_6)$alkoxycarbonyl and $(C_1$-$C_6)$acyl.

* * * * *